United States Patent

Ruker

[11] 4,218,112
[45] Aug. 19, 1980

[54] PHOTOMETER MICROSCOPE FOR MICROPHOTOMETER SCANNING OF FINE SPECIMEN STRUCTURES

[75] Inventor: Otto Ruker, Vienna, Austria

[73] Assignee: C. Reichert Optische Werke, AG, Vienna, Austria

[21] Appl. No.: 921,633

[22] Filed: Jul. 3, 1978

[51] Int. Cl.³ .............................................. G02B 21/00
[52] U.S. Cl. ...................................... 350/8; 350/285; 350/247; 250/234
[58] Field of Search ...................... 350/8, 19, 22, 6.3, 350/247, 285, 115, 116, 232, 6.1, 6.2, 86; 250/234, 235, 202, 203, 347

[56] References Cited

U.S. PATENT DOCUMENTS

| 3,254,227 | 5/1966 | Hock | 350/247 |
| 3,780,298 | 12/1973 | Agadzhanian et al. | 250/202 |

*Primary Examiner*—Jon W. Henry
*Attorney, Agent, or Firm*—Jeremiah J. Duggan; Alan H. Spencer; Stephen A. Schneeberger

[57] ABSTRACT

A positive and negative lens of equal power can provide the means to scan small objects being observed through a microscope if one of the lenses can be selectively decentered. The arrangement is particularly useful for microscopes having photometers that are used to analyze very small specimens, such as chromosomes, by scanning.

5 Claims, 6 Drawing Figures

PHOTOMETER MICROSCOPE FOR MICROPHOTOMETER SCANNING OF FINE SPECIMEN STRUCTURES

BACKGROUND OF THE INVENTION

The invention pertains to a photometer microscope with an apparatus for the microphotometer scanning of fine specimen-structures, which, in the ray-path between the objective and the photometer-part, exhibits an internal focusing lens Photometer microscopes with an apparatus for the microphotometer scanning of small specimen-structures are used for the study of diverse objects. One field of utilization, for instance, is a study of chromosomes, inasmuch as for some years now, methods exist with which it became possible to produce on chromosomes transverse stripes of different color intensity. This coloration makes it possible to reliably distinguish the chromosome-pairs from each other, and to correspondingly classify them.

The differences in the color intensity of the transverse stripes can be recognized with the naked eye only with great difficulty. For this reason photometer microscopes are used, which can measure and graphically record the different color intensities. For such an evaluation, it is required that the object to be studied be moved for microphotometer scanning, in order to be able to scan point by point the interesting parts of the object specimen in corresponding time sequence. The measured values are stored in a computer during scanning at the conclusion of the scanning, the information about the objects are computer evaluated and reported.

To produce the necessary relative movement, different devices have been used. In general, the procedure is to secure the object on a motor driven stage. The motors can be either direct current motors which are controlled by a joy-stick, or stepping motors can be used. In the first case, one gets a continuous, infinitely adjustable movement while in the second case, the step magnitude is not adjustable. With tasks with stepping motors, a minimal step size of 0.5 um is possible which is not sufficiently small for the study of chromosomes, because a step of 0.1 um is required. Consequently, work can only be done with a movable stage, if realtively coarse objects are to be studied.

Despite the use of a movable stage, in order to make possible a finer scanning, it is also known to electronically increase the number of measurements during one step of the stage. For example, if four measurements are taken during an 0.5 um step, effective distance is reduced to about 0.125 um. This procedure, can only be applied in one direction. Since the time available for a measurement by this system is naturally very short, evaluation of the results is difficult.

To overcome these problems the chromosomes or the like are first photographed and then evaluated from the photos thus obtained, which are larger than the originals, by the photometer microscope. It is obvious that this procedure also is not satisfactory, as it significantly increases time and errors can creep in, for instance, through defects of the photographic emulsion.

It is likewise known how to provide in the ray-path of the microscope between the objective and the photometer-part, an internal focusing lens, which moves the image past the measuring diaphragm (restrictor). This Method has the advantage that relatively small steps can be achieved, inasmuch as the already magnified image is now moved, hence the magnification factor of the objective can remain neglected. A disadvantage of the known arrangement, however is, above all, that through the additional lens, the ray-path of the microscope becomes altered, so that the microscope must be modified to accept the additional lens. Consequently, the known arrangement cannot find acceptance as an attachment for microscopes. Furthermore, it is proposed to move the lens by hand using a pantograph-like device. This has the substantial disadvantage that small, uniform movement cannot be achieved although such movement is not required because measurement takes place as a function of the position of the pantograph. Naturally, the disadvantage arises from this, that no continuous scanning of the specimen is possible, but only discrete areas, separated from each other, can be covered in any given case.

Finally, it is already known how to undertake an image-shift by optical means in the image field, for which purpose glass wedges or prisms, or rotatable or displaceable deflecting mirrors, operating opposite each other, are provided. Here also, however, the problem arises that the scanning steps, in general, do not become as fine as they are required to be. Additionally, devices having several prisms or deflecting mirrors are of a projecting nature so that only with difficulty if at all can they be brought into the microscope tube, and above all, they are not suitable for utilization as an attachment.

SUMMARY OF THE INVENTION

The present invention is based on a device for the microphotometer scanning of fine specimen-structures, which is constructed, so that the scanning can take place in fine steps in either direction. In addition, the possibility of a device constructed for the microphotometer scanning as an attachment which can be used without difficulties on existing microscopes.

According to the invention, a photometer microscope has a stationary compensating lens in the ray-path (axis) directly in front of or behind the internal focusing lens of the same focal power but opposite that of the internal focusing lens.

With the photometer microscope according to the invention, therefore, the displacement of the image occurs in front of the photometer diaphragm over an internal focusing lens inserted in series in the ray-path to the objective, whereby, despite relatively large displacement paths, an incremental displacements can be achieved when compared to the prior art. In spite of the presence of this internal focusing lens, however, the ray-path of the microscope in itself is not modified, because a compensating lens is provided. For the first time it is possible to equip a microscope with a scanning system for the displacement of the image in front of the photometer diaphragm. Both lenses, that is, the movable internal focusing lens and the stationary compensating lens, if they are directly adjacent to each other can be inserted without difficulty in the ray-path, for instance, in an attachment to an existing microscope.

DETAILED DESCRIPTION OF THE INVENTION

If the internal focusing lens and the compensating lens are arranged in the ray-path between the objective and a beam-splitter selectively positionable on the ray-path to effect a division of the light for the photometer and ocular which would have to be provided with a marking, for instance, a hair-cross or a graduated dial (plate), the possibility additionally exists of observing through the ocular the displacement of the image in front of the photometer diaphragm, so that it is possible to move the internal focusing lens mutually or with a special device, in such a manner that the movement of the specimen takes place along a predetermined track, for instance, a curved line.

A highly uniform movement, which is very desirable for computer-evaluation, can be obtained if the internal focusing lens is movable by a motor in a plane normal to the optical axis (ray-path). It is also advantageous for the drive to have two motors which move the internal focusing lens in perpendicular directions.

There are several types of motors which are appropriate for this purpose. However, it is especially favorable if the speed of rotation of both motors is continuously variable, for instance, as with direct-current motors. The motors may be controlled by a single control unit so that the movement of the internal focusing lens is at a uniform speed in all directions of movement. Then, the driving of the scanning beam, for instance on a curved line, is facilitated.

A preferred control for the motors is a control stick stick is ball mounted in a recess, it can be used for regulating the speed of both motors. Maximal deflection of the control stick provides the highest speed of movement and no deflection of the stick gives no movement so that displacement of the stick controls both the direction of movement as well as the speed of movement of both motors.

In order to achieve this, a so-called "joy-stick" is used, which can be constructed in such a way, that the control-stick displaces two potentiometers or the like positioned on perpendicular axes.

If a computer is used for the evaluation of the photometric measured signals it can also be used for the control of the motor drives for the interior focusing lens.

If, as is further provided according to the invention, the interior focusing lens and the compensating lens are arranged in an attachment which can be laterally inserted in a slot or some similar aperture of the microscope tube, the scanning device can be easily disconnected if no further movement is supposed to take place. Also, the slot or the aperture can be employed for the attachment of other attachments. When the housing of the additional lenses is an attachment, it is desirable that it contains the motors and other driving parts for movement of the focusing lens, because the driving elements can always remain linked with the interior focusing lens and thus, an adjustment once made can remain unchanged.

Finally, the fact lies within the scope of the invention that the housing, which takes the motors and other driving parts for the moving of the interior focusing lens, has on the top a display for showing the position of the interior focusing lens, for instance, to be able, without difficulties, to set the scanning beam before the start of the scanning, in reference to the specimen.

Further features, details and advantages of the invention are shown from the following description of a preferred embodiment, reference being made to the drawings.

THE DRAWINGS

DETAILED DESCRIPTION OF THE DRAWINGS

Figure 1:
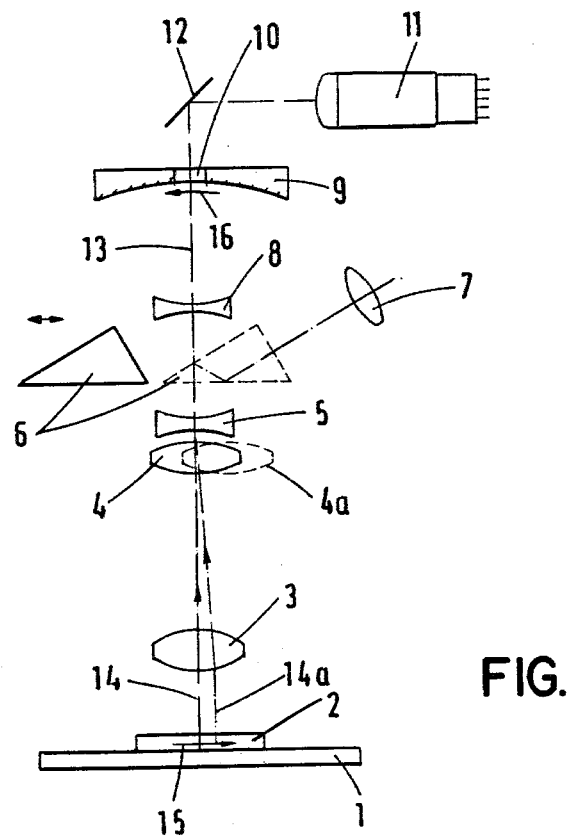
FIG. 1 is a diagram of a photometer microscope according to the invention.

The photometer microscope shown in FIG. 1 exhibits, as shown, a microscope stage 1, on which the specimen 2 is held. Along the ray-path (optical axis) 14 starting from specimen 2 in sequence, objective 3 of relatively high magnification, focusing lens 4, stationary lens 5, which is of the same focal power but of opposite sign to lens 4. Interior focusing lens 4 is a converging lens and compensating lens 5 is a diverging lens. Following compensating lens 5, light-beam passes through optional beam-splitter 6 to the ocular 7 and diverging lens 8, in front of mirror 9 having aperture 10 acting as a photometer diaphragm. Light passing through the diaphragm 10 then reaches detector 11. In the present case, a secondary-electron-multiplier is used, the light is deflected by mirror 12 to detector.

Beam-splitter 6 is normally located in the position indicated by the dotted line in FIG. 1. If, however, no visual observation is desired through ocular 7, it can be moved into the position shown in the solid line, in which case it is not located on optical axis 13. As is indicated in FIG. 1, interior focusing lens 4 can be moved from the position shown by the solid line, in which it is centered on the optical axis 13, into the dotted line position 4a. The consequence of this is, that for the scanning, the observation axis 14 lying on optical axis 13 is not used, but rather, alternate observation axis 14a displaced a small distance in the arrow-direction 15 is used. Consequently, an area of the specimen 2 is scanned, which is located to the right from the image-point scanned by the beam 14. In conjunction with movement of the internal focusing lens 4 to alternate location 4a, the sequence of images produced at measuring diaphragm 10 and detector 11 is a sequence of areas of specimen 2, along the direction arrow 15.

Figure 2:
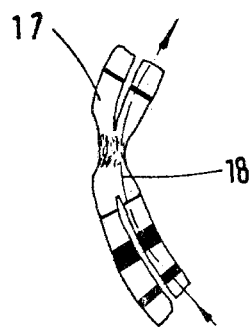
FIG. 2 is a top view of a stained chromosome to be studied.

The interior focusing lens 4 is moved by means of motors (not shown) in two directions, one perpendicular to the other, which directions lie in a plane, which is perpendicular to the optical axis 13. The shifting of the observation axis 14a for scanning in any direction afforded thereby. For example, chromosome 17 as shown in FIG. 2 may be scanned along the curved path indicated by the arrow 18, so that independent of the given curvature of the chromosome 17, a scanning takes place over its entire length, without observation beam 14a ever leaving the chromosome.

Figure 3:
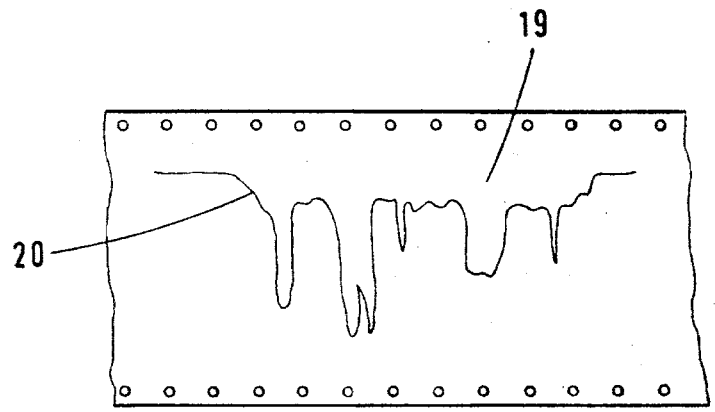
FIG. 3 is a representative curve of the measured photometric values.

In conjunction with such scanning and recording of the measured signals of photo multiplier 11 in a recorder, we obtain on paper 19 curve 20 as shown in FIG. 3. The curve 20 gives information concerning the differential coloration of chromosome 17 along the path 18. From curve 20, conclusions can then be reached concerning the specific features of specimen 2.

Figure 4:
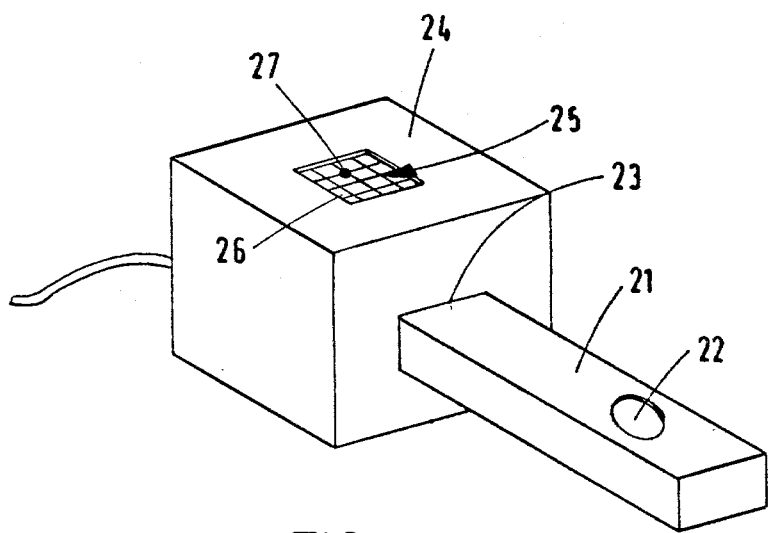
FIG. 4 shows an attachment having the interior focusing lens, compensating lens, and their drive means.

Another possibility is, naturally, to feed signals of the photo multiplier 11 into a computer, which then expresses corresponding values after the conclusion of the measuring procedure, based on a given program. As was already mentioned above, it is possible in conjunction with the photometer microscope in accordance with the invention, to construct interior focusing lens 4 and compensating lens 5 together with the driving elements for lens 4, as an attachment. FIG. 4 shows the appearance of such an attachment. This device comprises insert 21 which in the embodiment shown is constructed in a rectangular shape and size chose to fit in a recess in the microscope tube (body). Such recesses presently exist for receiving analyzers contract interference devices, or the like. The insert 21 has two apertures 22 (one shown) in alignment between which lenses 4, 5 are arranged. When using attachment shown in FIG. 4 insert 21 is positioned so that apertures 22 and lenses 4, 5 are located on the optical axis 13 of the microscope.

On distal end 23 of insert 21, a housing 24 is located to contain driving elements (not shown) for internal focusing lens 4, for instance, two motors and the corresponding linkage rods. Inasmuch as the construction of these driving elements are well known, it does not seem necessary here to further describe them. It is only essential to point to the fact that on the upper side of the housing 24, as FIG. 4 shows, a display 25 is provided to indicate the position of internal focusing lens 4. Display 25 encompasses a scan pattern plate 26, the position of internal focusing lens 4 is then indicated by point 27.

The drive of the internal focusing lens 4 can take place in the most varied ways. For instance, it would be possible to move the internal focusing lens 4 by one or more stepping motors. It is preferred however, if movement of lens 4 is possible in such a way that scanning along line 18 in FIG. 18 is possible. This can be accomplished in a simple manner by the use of two direct-current motors which provide movement of internal focusing lens 4 in X and Y directions and permit the rotational speed of these motors to be independently variable.

Figure 5:
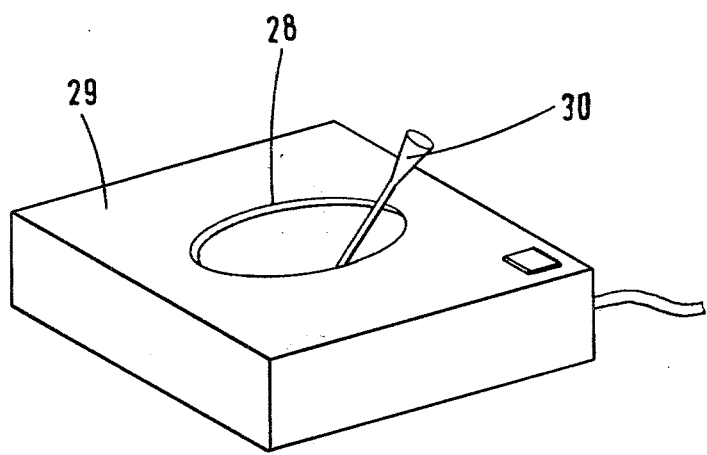
FIG. 5 shows a device for controlling the movement of the interior focusing lens.
Figure 6:
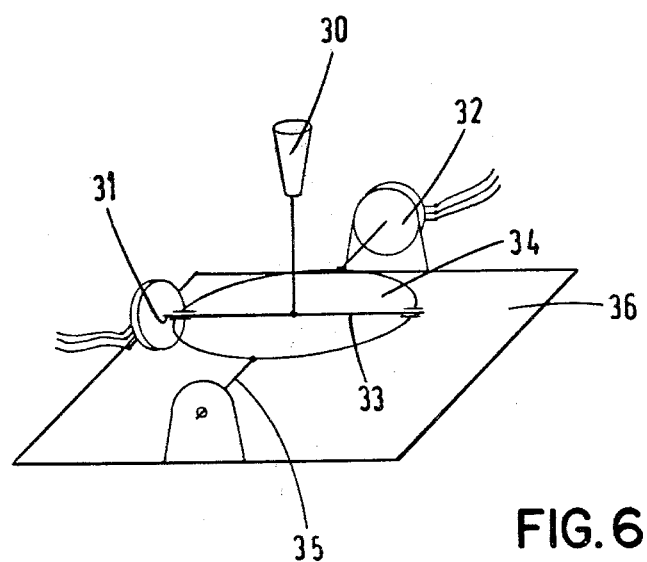
FIG. 6 is a sketch illustrating the operation of the control device of FIG. 5.

In FIGS. 5 and 6, a device is shown, which can be used for the controlling two such direct-current motors. This device comprises a joy-stick 30, mounted in circular aperture 28 of cover plate 29 and which can move on all sides. The movements of joy-stick 30, are transmitted, corresponding to its direction and amount of deflection, to two potentiometer 31, 32 or equivalent control-elements for varying the input to a respective servo-motor. From FIG. 6, it can be seen that the joy-stick 30 is attached to carrier 33, which is rotatably mounted in pivotable carrier 34 axis of rotation for carrier 33 is normal to axis 35 of carrier 34. Base plate 36 supports pivotable carrier 34.

Carrier 34 is connected to the tap of potentiometer 32 along axis 35 so that rotation of carrier 34 about axis 35 causes corresponding change in the output of potentiometer 32. In a similar manner, carrier 33, acts on the control element of potentiometer 31, which is supported by carrier 34.

In this way, a device provides change of the rotational speed of either or both of motors controlled by potentiometers 31, 32 corresponding to movement of the joy-stick 30. According to FIG. 5 joy-stick 30 is positioned in aperture 28, which is essentially spherical. The microscopist therefore has the ability to vary the speed and direction of movement of the internal focusing lens 4, by the direction and extent of deflection of the joy-stick 30 while observing through the ocular and lens 4 on the display.

What is claimed is:

1. A scanning system for a microscope which comprises, a pair of lenses on an optical axis each of said pair having equal and opposite power, one of said pair being movable in a plane normal to the optical axis, a gimbal mounted joy-stick to control movement of said one of said lenses.

2. The scanning system according to claim 1 wherein said lenses are adjacent and said one of said pair is a positive lens.

3. The scanning system according to claim 1 further including means to display the position of said one of said pair of lenses relative to the optical axis.

4. In combination, an optical microscope having an optical axis, an attachment for said microscope, said attachment including a positive lens and a negative lens aligned on an attachment axis, one of said positive and negative lenses being selectively movable from a normal position in a plane perpendicular to said attachment axis, a gimbal mounted stick means to move said one of positive and negative lenses in XY directions which lie in said plane and means for connecting said attachment to said microscope with said optical and attachment axes being coincident.

5. The combination according to claim 4 wherein said microscope has an objective, and a photometer and said means is located between said objective and said photometer.

* * * * *